United States Patent [19]

Baumgarten

[11] Patent Number: 5,139,789
[45] Date of Patent: Aug. 18, 1992

[54] CARDIOPLEGIA SOLUTIONS THAT PREVENT HEART CELL SWELLING

[75] Inventor: Clive M. Baumgarten, Richmond, Va.

[73] Assignees: Virginia Commonwealth University, Richmond; Center for Innovative Technology, Herndon, both of Va.

[21] Appl. No.: 599,014

[22] Filed: Oct. 17, 1990

[51] Int. Cl.$^5$ .............................................. A61K 33/14
[52] U.S. Cl. ................... 424/678; 424/677; 424/679; 424/680; 424/681
[58] Field of Search .............. 414/677, 678, 679, 680, 414/681

[56] References Cited

U.S. PATENT DOCUMENTS 4,649,050  3/1987  Veech .................................. 424/678
4,923,442  5/1990  Segall et al. ........................ 424/667

OTHER PUBLICATIONS

Spring KR, Persson BE. In: Epithelial Ion and Water Transport, eds: ADC Macknight, JP leader, Raven Press, New York, pp. 15-21, 1981.
Desilets M, Baumgarten CM., Am J. Physiol., 251:C197-C208, 1986.
Poole RC, Halestrap AP, Price SJ, Levi AJ, Biochem J., 264:409-418, 1989.
Gibbons, WR, Fozzard HA, J. Gen. Physiol., 65:345-365, 1975.
Rasmussen HH, Singer DH, Ten Eick RE, Am. J. Physiol., 251:H331-339, 1986.
Glitsch HG, Pusch H, Pfluegers Arch., 402-109-115, 1984.
Tyers GFO in A Textbook of Clinical Cardioplegia, eds. RM Engelman. S. Levitsky, Futura Publishing, Mt. Kisco, 1982, pp. 139-155.
Hearse DJ, Braimbridge MV, Jynge P, Protection of the Ischemic Myocardium: Cardioplegia, Raven Press, New York, 1981, pp. 209-213, 224-228, 230-231, 246-252.
Baumgarten CM, Fozzard HA in The Heart and Cardiovascular System, eds. HA Fozzard, E Haber, RB Jennings, AM Katz, HE Morgan, Raven Press, New York, 1986, pp. 601-626.
Schnabel PA, Gebhard MM, Pomykai T, Schmiedl A, Preuβe CJ, Richter J, Bretschneider HJ, Thorac, Cardiovasc. Surgeon, 35:148-156, 1987.
New Eng. J. Med., 283:1285, 1970.
T. Yeh, et al., *Ann. Thorac Surg.*, "Superior Myocardial Preservation with Modified UW Solution . . . ," 49; pp. 937-939 (1990).
W. Gray, *Ann. Thorac Surg.*, "Potassium-Induced Cardioplegia," 20(1) pp. 95-100 (1975).
W. N. Wicomb et al., *Transplantation Proceedings*, "Improved Cardioplegia Using New Perfusates," 21(1) pp. 1357-1358 (1989).
R. Ferreira et al., *Ann. Thorac Surg.*, "Reduction of Reperfusion Injury with Mannitol Cardioplegia," 48, pp. 77-84 (1989).
E. Krohn, et al., *Pflugus Arch*, "The Cardioplegic Solution 117k" 415 pp. 269-275 (1989).

*Primary Examiner*—Richard L. Raymond
*Assistant Examiner*—Mark W. Russell
*Attorney, Agent, or Firm*—Whitham & Marhoefer

[57] ABSTRACT

Cardioplegia solutions having potassium and chloride ion concentrations selected to give a product approximately equal to the product of the potassium and chloride ion concentrations in blood and blood substitutes have been shown to prevent heart cell swelling during cardioplegia.

10 Claims, 2 Drawing Sheets

CARDIOPLEGIA SOLUTIONS THAT PREVENT HEART CELL SWELLING

DESCRIPTION

Background of the Invention

1. Field of the Invention

The subject invention is generally related to cardioplegia solutions which are used to stop and protect the heart during surgery and to preserve the heart or other organs while they are transported or prepared for transplantation. More particularly, the cardioplegia solutions contemplated by this invention have controlled potassium and chloride ion concentrations such that heart cell swelling is minimized.

2. Description of the Prior Art

Cardioplegia solutions are specially designed solutions which are used during cardiac surgery to arrest the heart beat and to place the heart in a state wherein the muscle is relaxed and is at least partially protected from the damaging effects of oxygen deprivation. In present surgical practice, the temperature of the heart is lowered from the normal body temperature of 37° C. to a temperature between 5° C. and 10° C. while perfusing the heart with a cold cardioplegia solution having elevated levels of potassium. The cold temperatures and the elevated levels of potassium act in combination to stop and protect the heart during surgery and, typically, these same conditions are used when transporting the heart or other organs for transplantation operations. Several different cardioplegia solutions are currently available and different techniques for using cardioplegia solutions are in common practice. For example, cardioplegia solutions often have varying amounts of potassium, magnesium, and several other minor components. In some cardioplegia solutions, sodium is replaced with potassium. Sometimes drugs are added to the cardioplegia solution to aid in muscle relaxation and protection from ischemia and some surgeons have found varying the temperature at which the cardioplegia solution is used can have beneficial effects. A common feature of most cardioplegia solutions now in use is that they have elevated levels of potassium and chloride is the principle anion.

Heart cell swelling (edema) may occur during cardioplegia induced cardiac arrest. It is widely thought that heart cell swelling, in addition to other factors, can cause cardiac cell damage which leads to a diminution in normal cardiac function. In severe cases, damage may preclude the surgeon from restarting the heart and ultimately in the death of the patient. Therefore, a need exists for a cardioplegia solution which can prevent heart cell swelling during surgery and transportation of the organ for transplantation purposes.

SUMMARY OF THE INVENTION

It is therefore an object of the present invention to provide a solution which prevents heart cell swelling during cardioplegia and during transplantation of organs.

It is another object of this invention to provide a cardioplegia solution which includes controlled potassium and chloride ion concentrations.

According to the invention, experiments have been performed which show that heart cell swelling during cardioplegia can be minimized by using cardioplegia solutions having concentrations of potassium and chloride ion that are selected in accordance with the potassium and chloride ion concentrations found in blood or blood substitutes. In particular, it has been found that swelling is prevented if the product of the concentrations of potassium $[K^+]$ and chloride $[Cl^-]$ ions in the cardioplegia solution is approximately equivalent to the product of the concentrations of potassium and chloride ions in blood or blood substitute solutions. This relationship is illustrated by Equation 1:

$$[K^+][Cl^-](\text{in card. sol.}) = [K^+][Cl^-](\text{in blood}) \quad [Eq.1]$$

The potassium ion concentration $[K^+]$ of cardioplegia solutions must be relatively higher than that found in blood since it serves the functions of stopping the heart beat and protecting the heart during surgery. Therefore, the product relationship shown above in Equation 1 is maintained by substituting a different anion for a portion of the chloride anion $[Cl^-]$ typically found in most cardioplegia solutions.

BRIEF DESCRIPTION OF THE DRAWINGS

The foregoing and other objects, aspects and advantages will be better understood from the following detailed description of the preferred embodiment of the invention with reference to the drawings, in which.

DETAILED DESCRIPTION OF A PREFERRED EMBODIMENT OF THE INVENTION

Figure 1:
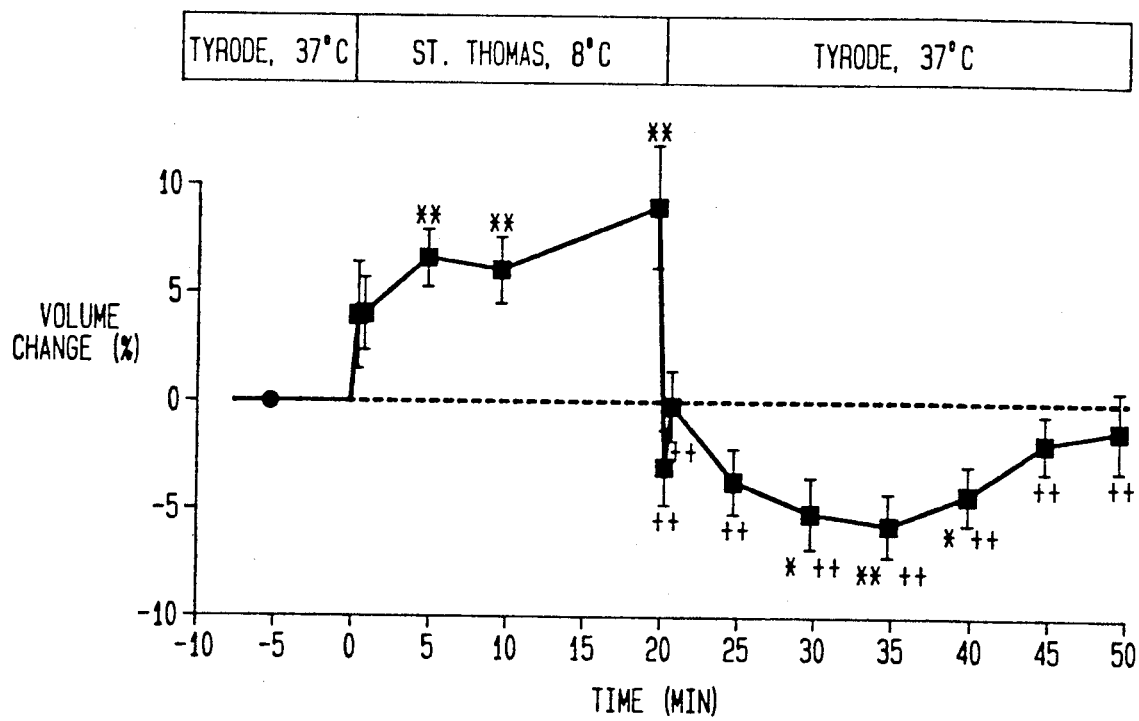
FIG. 1 is a graph showing the volume change versus time of heart cells treated with a standard cardioplegia solution.

Experiments have been performed using ventricular heart cells from rabbits. In the experiments, the volume of single, isolated heart cells was measured using videomicroscopy before, during and after exposure of the cells to cardioplegia and control solutions. Videomicroscopy is a well known technique for measuring the volume of a cell and involves making dimensional measurements of the cell under the microscope and calculating the volume from the dimensional measurements. Spring et al., in *Epithelial Ion and Water Transport*, eds: ADC Macknight, JP leader, Raven Press, New York, pp 15-21, 1981, provides a description of the method for measuring cell volume by video-microscopy. The ventricular heart cells from rabbits were prepared by standard enzymatic isolation procedures such as those described in Desilets et al., *Am. J. Physiol.* 251:C197-C208, 1986, and Poole et al., *Biochem J.* 264:409-418, 1989. The heart is excised and attached to a Langendorff perfusion apparatus and the aorta is perfused with a physiological solution modified to contain a low concentration of calcium and the enzymes collagenase and protease. After 10-20 min of perfusion, the heart is cut into small strips and single viable cells are released by gentle aggitation. Single heart cells have proven to be useful for studying a wide variety of physiological phenomena. After isolation, the cells are washed with a physiological solution and placed in a glass-bottom chamber on the stage of an inverted microscope. Cells are observed through a video camera attached to the microscope. A computerized image analysis system is used to measure cell dimensions. The solutions required to bathe the cells are heated or cooled in several heat-exchangers, and a selected solution is gently flushed through the chamber by gravity. This maintains the temperature of the cells in the chamber at selected levels (e.g., 8° C. or 37° C.), and switching an inlet valve changes the solution bathing the cells.

To simulate surgical operations, the heart cells were perfused with a blood substitute control solution which does not have cardioplegia activity at 37° C. for a first period of time, then the heart cells were cooled to 8° C. while perfusing with a cold cardioplegia solution and the effects on cell volume were observed for a second period of time, then the heart cells were warmed to 37° C. while perfusing with the blood substitute control solution for a third period of time.

The control solution used in the experiments was Tyrode's solution which contained the following constituents in millimolar (mM) concentrations:

130 mM NaCl
5 mM KCl
2.5 mM $CaCl_2$
1.75 mM $Na_2HPO_4$
1.2 mM $MgSO_4$
24 mM $NaHCO_3$

The Tyrode's solution had a pH of 7.4 at 37° C. and was equilibrated with a 95% $O_2$/5% $CO_2$ gas mixture in order to saturate the solution with oxygen and to make the concentration of $CO_2$ in the solution the same as in blood. The osmolarity of the Tyrode's solution was verified with a freezing point depression osmometer and was the same as the cardioplegic solutions. This ensures that any volume changes are due to the composition of the solutions rather than variations in their osmolarities. As can be calculated from the listing of components in the Tyrode's solution, the potassium ion concentration is $[K^+]=5$ mM and the chloride ion concentration is $[Cl^-]=140$ mM. Therefore, the product $[K^+][Cl^-]$ for Tyrode's solution is equal to 700 $mM^2$.

While it is known that the normal values for blood are $[K^+]=3.5$ to 5 mM and $[Cl^-]=100$ to 106 mM (see, New Eng. J. Med. 283:1285, 1970) for a $[K^+][Cl^-]$ product ranging between 350 and 530 $mM^2$, the difference in potassium $[K^+]$ and chloride $[Cl^-]$ concentrations between blood and Tyrode's solution should not affect the manner in which Tyrode's solution mimics the activity of blood. Tyrode's solution is a well known physiological saline solution that is commonly used as a substitute for blood in physiological experiments on heart cells (see, e.g., Desilets et al., Am. J. Physiol., 251:C197–C208, 1986, Gibbons et al., J. Gen. Physiol., 65:345–365, 1975, and Rasmussen et al., Am. J. Physiol., 251:H331–339, 1986). The chief differences between blood and Tyrode's solution is that blood contains quantities of dissolved proteins not contained in Tyrode's solution and Tyrode's solution contains a slightly higher concentration of chloride [Cl] than blood. Tyrode's solution has the experimental advantages over blood that cells in Tyrode's solution can be viewed more easily under a microscope, the researcher is not required to handle a blood sample, and the concentration of constituents in Tyrode's solution can be precisely determined whereas in blood the concentrations are never precisely known.

The prior art cardioplegia solution used in the experiments was a variant of St. Thomas solution. St. Thomas solution is a standard cardioplegia solution in common use in surgery today and contains the following constituents:

| | |
|---|---|
| 110 mM NaCl | 10 mM $NaHCO_3$ |
| 16 mM KCl | 16 mM $MgCl_2$ |
| 1.2 $CaCl_2$ | |

The St. Thomas solution had a pH of 7.3 at 9° C. and was equilibrated with a 95% $O_2$–5% $CO_2$ gas mixture. The osmolarity of the St. Thomas solution was verified with a freezing point depression osmometer. As can be calculated from the above listing of constituents in the St. Thomas solution, the potassium ion concentration $[K^+]$ is 16 mM, the chloride ion concentration $[Cl^-]$ is 160.4 mM, and the product of the potassium ion concentration and chloride ion concentration is $[K^+][Cl^-]=2566.4$ $mM^2$.

The present invention is concerned with matching the $[K^+][Cl^-]$ product in the cardioplegia solution with that found in the blood or blood substitute which in the present case is Tyrode's solution and which has a $[K^+][Cl^-]$ product equal to 700 $mM^2$. Therefore, a low $[Cl^-]$ St. Thomas solution having low chloride ion concentration was prepared for the experiments by substituting an equimolar amount of sodium methanesulfanate for all the sodium chloride and potassium methanesulfanate for part of the potassium chloride in the prior art variant of St. Thomas' solution listed above. The low $[Cl^-]$ St. Thomas solution had the following constituents:

| | |
|---|---|
| 110 mM $NaMeSO_4$ | 10 mM $NaHCO_3$ |
| 16 mM $MgCl_2$ | 9.35 mM KCl |
| 6.65 mM $KMeSO_4$ | 1.2 mM $CaCl_2$ |

The low $[Cl^-]$ St. Thomas solution had a pH of 7.3 at 8° C. and was equilibrated with a 95% $O_2$-5% $CO_2$ gas mixture. The osmolarity of the low chloride variant of St. Thomas solution was verified with a freezing point depression osmometer. As can be calculated from the above listing of constituents in the low $[Cl^-]$ St. Thomas solution, the potassium ion concentration $[K^+]$ remains at 16 mM; however, the chloride ion concentration $[Cl^-]$ has been adjusted to 43.75 mM, so that the product of the potassium ion concentration and chloride ion concentration is $[K^+][Cl^-]=700$ $mM^2$ which is equal to $[K^+][Cl^-]$ product in the Tyrode's solution.

FIG. 1 shows the effect of cardioplegia using the above-described prior art variant of St. Thomas solution. The heart cells began to swell immediately upon starting the cardioplegia conditions of 8° C. and perfusion with St. Thomas solution. Over a short period of time, the cells swelled by approximately as much as nine percent. The swelling caused by the cardioplegia solution may cause damage to the myocardium and occlude the coronary arteries of a patient who is being operated on that would prevent successful restarting the heart. When the Tyrode's solution was readmitted, the cells shrank to less than their initial size and then slowly returned to their initial volume.

Figure 2:
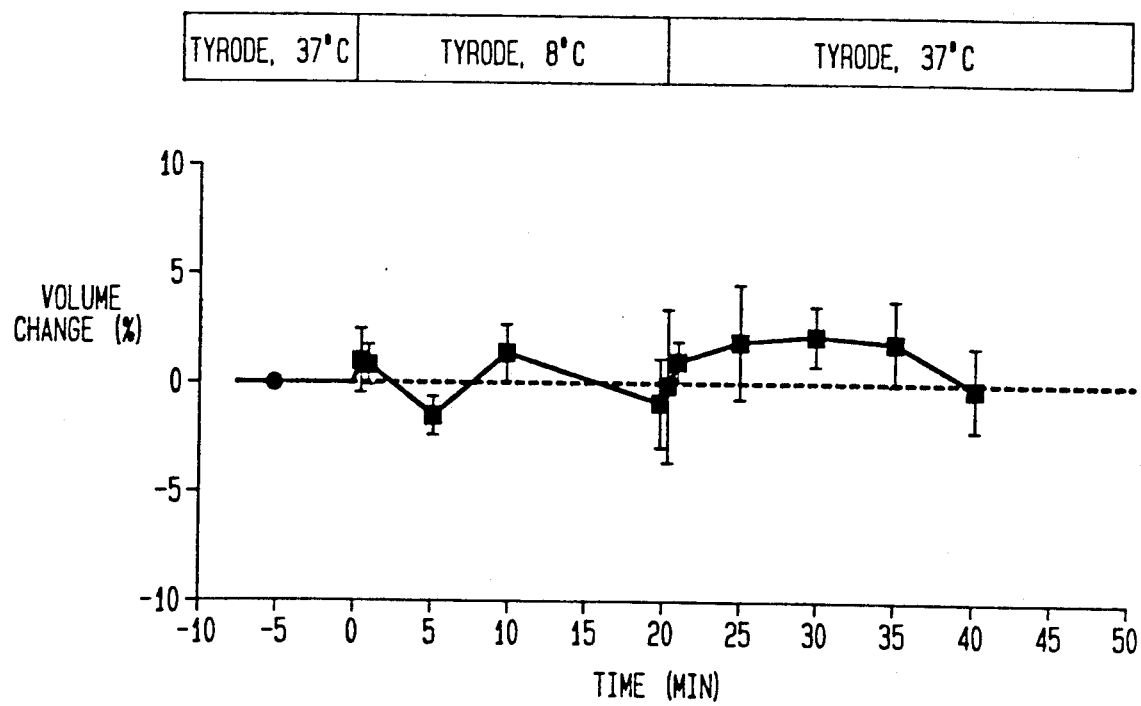
FIG. 2 is a graph showing the volume change versus time of heart cells subjected to a physiological solution at different temperatures.

FIG. 2 shows that when the heart cells are exposed only to Tyrode's solution at the varying temperatures which would occur in surgery, i.e., 37° C. is body temperature and 8° C. approximates the temperature at which heart surgery would occur, the cells do not swell. Hence, FIG. 2 shows that the swelling and shrinkage of the heart cells exhibited in FIG. 1 is due to the St. Thomas cardioplegia solution and not due to cooling the heart cells. It is reiterated here that cold Tyrode's solution merely mimics the response of blood and that Tyrode's solution does not meet the requirements of a cardioplegia solution and could not be used as a cardioplegia solution. The composition of Tyrode's solution mimics blood and is intended to maintain the heart beat. Cardioplegic solutions are intended to arrest the heart in diastole, a relaxed state, and cardioplegic solutions contain a much higher potassium concentration and usually a much higher magnesium concentration than Tyrode's solution or blood. Certain deviations of the ion concentrations in cardioplegic solutions from physiological ion concentrations, such as those of Tyrode's solution, are required for the protective effect of cardioplegic solutions.

Figure 3:
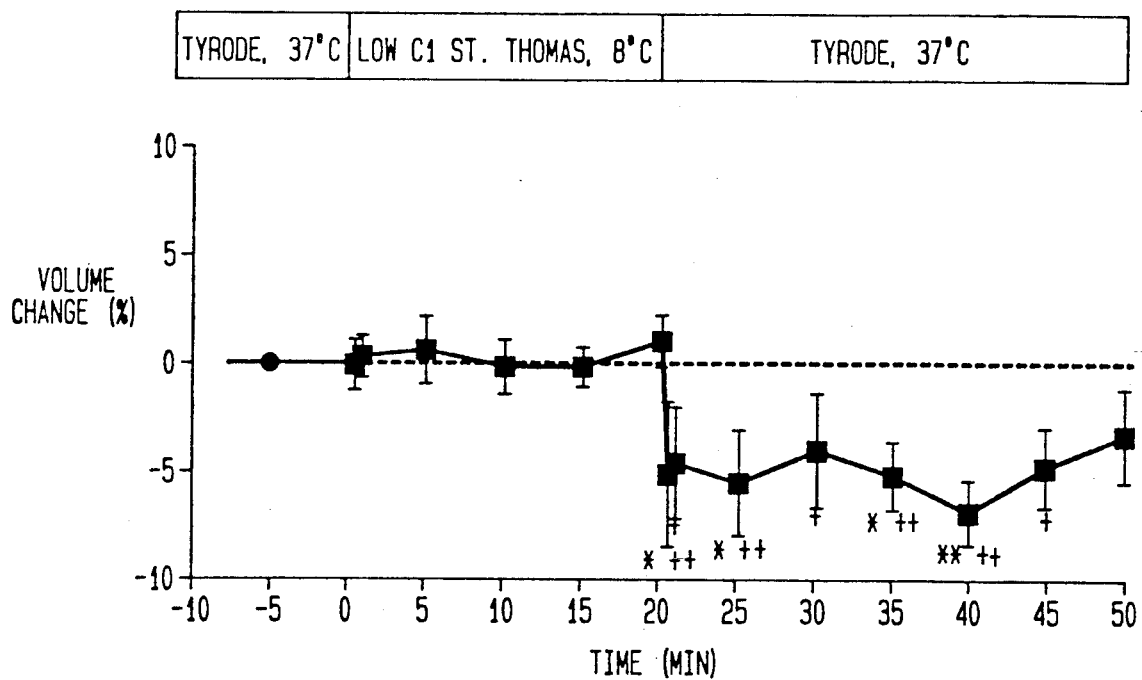
FIG. 3 is a graph showing the volume change versus time of heart cells treated with a cardioplegia solution according to the present invention.

FIG. 3 shows the effects of the low [Cl$^-$] St. Thomas solution on the heart cells. FIG. 3 shows that the cell volume is unaffected during the cardioplegia. However, cell volume decreases on rewarming in Tyrode solution. This shrinkage is caused by the well known phenomena of sodium being pumped out of the cell by the sodium-potassium pump upon rewarming (see, e.g., Rasmussen et al., *Am. J. Physiol.*, 251:H331–339, 1986 and Glitsch et al., *Pfluegers Arch.*, 402:109–115, 1984). At the end of these experiments, heart cell volume was statistically indistinguishable from the original value.

Figure 4:
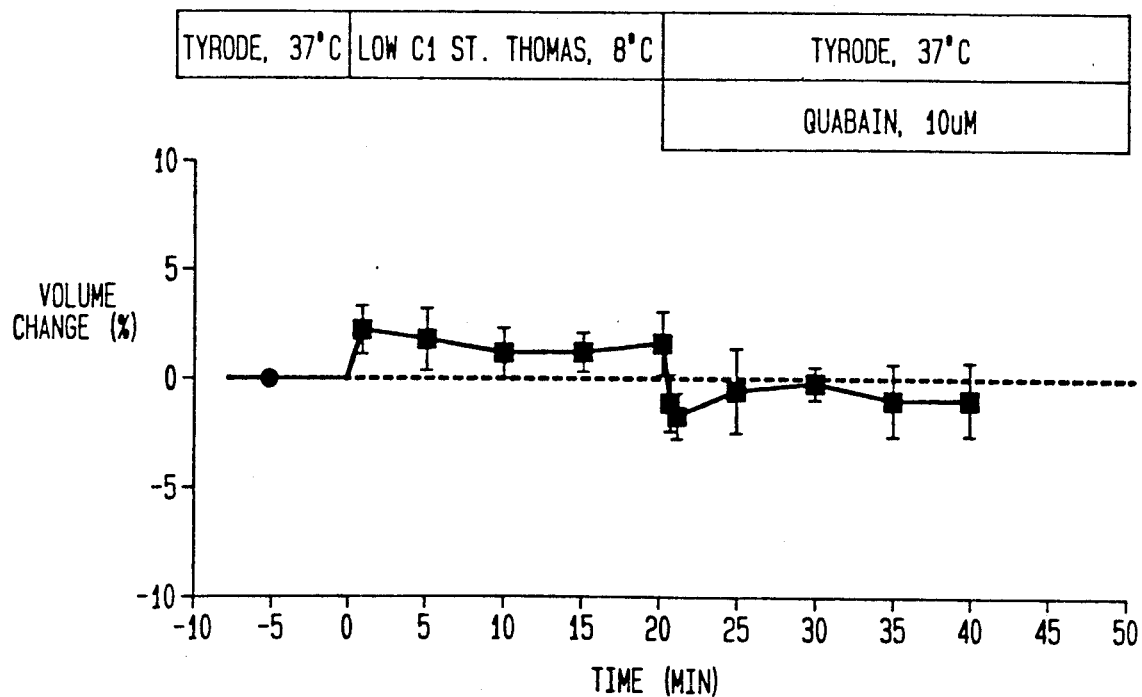
FIG. 4 is a graph showing the volume change versus time of heart cells treated with a cardioplegia solution according to the present invention and then with a compound that inhibits the sodium-potassium pump.

FIG. 4 proves that the shrinkage shown in FIG. 3 is in fact due to the activity of the sodium potassium pump. Like the cells in the experiment shown in FIG. 3, the cells in the experiment shown in FIG. 4 were treated with a [Cl$^-$] Thomas solution, but 10 $\mu$M of ouabain, a well known inhibitor of the sodium-potassium pump, was added to the Tyrode's solution used for rewarming from a concentrated aqueous stock solution. As before, the cells did not swell during cardioplegia. After cardioplegia, ouabain clearly halted the shrinkage due to the activity of the sodium-potassium pump. The shrinkage due to the sodium-potassium pump can be avoided by reducing the entry of sodium during cardioplegia. For other reasons, the potentially beneficial effects of reducing sodium entry has been discussed in the literature (see, e.g., Tyers, *A Textbook of Clinical Cardioplegia*, Eds. Engelman et al., Futura Publishing, Mt. Kisco, 1982, pp. 139–155 and Hearse et al., *Protection of the Ischemic Myocardium: Cardioplegia*, Raven Press, New York, 1981, pp. 209–213, 224–228, 230–231, 246–252). This component of the results is merely shown to fully establish the basis for the observed changes in volume.

The experiments clearly show that a cardioplegia solution having a [K$^+$][Cl$^-$] product matched to that of blood or a blood substitute will prevent the potentially damaging effects of cell swelling caused by prior art cardioplegia solutions. Since blood has a known [K$^+$][Cl$^-$] product of 350 to 500 mM$^2$, cardioplegia solutions should contain appropriate concentrations of potassium and chloride ions to fall within this range. Typically, cardioplegic solutions utilize potassium concentrations of 10 to 30 mM to partially depolarize the cell membrane and acheive arrest of the heart. As shown by Baumgarten et al., in *The Heart and Cardiovascular System.*, Eds. Fozzard et al., Raven Press, New York, 1986, pp. 601–626, modification of the chloride concentration does not effect the response of heart cells to potassium concentrations in this range.

It is contemplated that suitable cardioplegia solutions can be produced by substituting a different anion for a portion of the chloride anion [Cl$^-$] typically found in most cardioplegia solutions. The substituted anion should be poorly permeable or impermeable to cardiac cell membrane, and it should have a low pKa so that negligible amounts of anion are protonated (which would allow them to permeate the membrane in uncharged form). If the substituted anion was permeable, as is chloride, it would enter the cell under the conditions of cardioplegia. Such entry of anions would disrupt the osmotic balance between the inside of the cell and the media bathing the cell, would cause water to enter the cell, and would cause cell swelling. Suitable examples of anions would include methanesulfanate and isethionate anion; however, substitution of other anions should provide similar results and would maintain the product equivalency relationship. The basis for the effect of these ions on volume regulation is thought to be the tendency of permeable ions to distribute according to electrochemical equilibrium. That is to say, permeable ions will diffuse from areas of high concentration to areas of low concentration, and positively charged ions such as potassium will diffuse towards regions of negative potential, while negatively charged ions such as chloride will diffuse towards regions of positive potential. Inside a heart cell, the concentration of potassium is high and the concentration of chloride is low; in physiological solutions and blood, the concentration of potassium is low and the concentration of chloride is high; and the potential inside a cell, called the membrane potential (Em), is negative with respect to the outside. The membrane potential influences the distribution of both potassium and chloride. If both ions reach their electrochemical equilibrium, the energy available in the electrical gradient would equal that available in the concentration gradient, and the relationship described in equation 2 would hold:

$$E_m = RT/F\ ln([K^+]_i/[K^+]_o) = RT/F\ ln([Cl^-]_o/[Cl^-]_i) \qquad \text{Eq. 2}$$

where R is the gas constant, F is Faraday's constant, T is temperature in degrees Kelvin, and subscripts i and o refer to the concentrations inside and outside a cell, respectively. At any value of $E_m$, dividing both sides by RT/F and taking the antilogs gives:

$$[K^+]_i/[K^+]_o = [Cl^-]_o/[Cl^-]_i \qquad \text{Eq. 3}$$

which can be rearranged to give equation 1. Equation 2 predicts that potassium and chloride will enter heart cells under cardioplegic conditions as presently practiced and exemplified by St. Thomas' solution As these ions enter the cell, the osmotic balance will be disturbed and water will follow resulting in cell swelling. Equation 2 also predicts that ions will not redistribute when potassium in a perfusate is raised if chloride is lowered at the same time so that the [K][Cl] product is constant. This equation also predicts the magnitude of ion and, consequently, water movements if the [K$^+$][Cl$^-$] product is not maintained equal but varied in an arbitrary mannor. Because previous research (see, e.g., Schnabel et al., *Thorac. Cardiovasc. Surgeon.* 35:148–156, 1987) indicates that damage to the heart is less severe or is reversible when cardiac swelling is minimal (e.g., 1%), small deviations from exact [K+][Cl−] product equivalency may occur without lessening the beneficial aspects of this invention.

While the invention has been described in terms of its preferred embodiment where the product of [K+][Cl−] in a cardioplegia solution is equivalent to the product of [K+][Cl−] in blood or a blood substitute, those skilled in the art will recognize that the invention can be practiced with modification within the spirit and scope of the appended claims.

Having thus described my invention, what I claim as new and desire to secure by Letters Patent is as follows:

1. A cardioplegia solution comprised of a mixture of sodium methanesulfonate, sodium bicarbonate, magnesium chloride, potassium chloride, potassium methanesulfonate, and calcium chloride, wherein the concentrations of said sodium methanesulfonate, sodium bicarbonate, magnesium chloride, potassium chloride potassium methanesulfonate, and calcium chloride are chosen such that said cardioplegia solution includes potassium ions of a first concentration and chloride ions of a second concentration and a product of said first concentration of potassium ions and said second concentration of chloride ions in said cardioplegia solution is approximately equal to the product of the concentrations of potassium and chloride ions in a patient's blood, said potassium ion concentration in said cardioplegia solution being greater than said potassium ion concentration in said patient's blood, said chloride ion concentration in said cardioplegia solution being less than said chloride ion concentration in said patient's blood.

2. A cardioplegia solution as recited in claim 1 wherein said product ranges between 350 mM$^2$ and 700 mM$^2$.

3. A cardioplegia solution as recited in claim 1 wherein said potassium ion concentration is 16 mM.

4. The cardioplegia solution of claim 1 wherein said potassium ion concentration is at least 16 mM.

5. A method of adapting an existing cardioplegia solution including potassium ions of a first concentration and chloride ions of a second concentration to produce a second cardioplegia solution with a third concentration of potassium ions and a fourth concentration of chloride ions which exhibits reduced heart cell swelling, comprising the step of substituting constituents with chloride anions in said existing cardioplegia solution with constituents not having chloride anions thereby producing said second cardioplegia solution in which a product of said third concentration of potassium ions and said fourth concentration of chloride ions in said cardioplegia solution is approximately equal to the product of the concentrations of potassium ions and chloride ions in a patient's blood, said potassium ion concentration in said cardioplegia solution being greater than said potassium ion concentration in said patient's blood, said chloride ion concentration in said cardioplegia solution being less than said chloride ion concentration in said patient's blood.

6. A method as recited in claim 5 wherein said first concentration of potassium ions in said existing cardioplegia solution and said third concentration of potassium ions in said second cardioplegia solution produced by said step of substituting are equivalent.

7. A method of using cardioplegia solutions for surgery and organ transport, comprising the steps of:
   determining a potassium ion concentration and a chloride ion concentration in a patient's blood;
   calculating a product of said potassium ion concentration and said chloride ion concentration in said patient's blood; and
   matching a cardioplegia solution capable of interrupting myocardium contractions to said product of said potassium ion concentration and said chloride ion concentration in said patient's blood by having said cardioplegia solution include a potassium ion concentration and chloride ion concentration with a product approximately equivalent to said product of said potassium ion concentration and said chloride ion concentration in said patient's blood, said potassium ion concentration in said cardioplegia solution being greater than said potassium ion concentration in said patient's blood, said chloride ion concentration in said cardioplegia solution being less than said chloride ion concentration in said patient's blood.

8. A method as recited in claim 7 wherein said step of matching includes the step of using anions which are poorly permeable to cardiac cell membrane and have a low pKa to reduce said chloride ion in said cardioplegia solution.

9. A method of using cardioplegia solutions for surgery and organ transport, comprising the steps of:
   determining a potassium ion concentration and a chloride ion concentration in a physiologic blood substitute;
   calculating a product of said potassium ion concentration and said chloride ion concentration in said physiologic blood substitute; and
   matching a cardioplegia solution capable of interrupting myocardium contractions to said product of said potassium ion concentration and said chloride ion concentration in said physiologic blood substitute by having said cardioplegia solution include a potassium ion concentration and chloride ion concentration with a product approximately equivalent to said product of said potassium ion concentration and said chloride ion concentration in said physiologic blood substitute, said potassium ion concentration in said cardioplegia solution being greater than said potassium ion concentration in said physiologic blood substitute, said chloride ion concentration in said cardioplegia solution being less than said chloride ion concentration in said physiologic blood substitute.

10. A method as recited in claim 9 wherein said step of matching includes the step of using anions which are poorly permeable to cardiac cell membrane and have a low pKa to reduce said chloride ion in said cardioplegia solution.

* * * * *